United States Patent [19]

Motta

[11] 4,286,092
[45] Aug. 25, 1981

[54] 5-AMINO-4-CHLORO-2-PHENYL-3(2H)-PYRIDAZINONE FREE FROM 5-CHLORO-4-AMINO-2-PHENYL-3(2H)-PYRIDAZINONE, AS A SELECTIVE WEED-KILLER

[75] Inventor: Raimondo Motta, Milan, Italy

[73] Assignee: Oxon Italia S.p.A., Milan, Italy

[21] Appl. No.: 49,654

[22] Filed: Jun. 19, 1979

[30] Foreign Application Priority Data

Jun. 22, 1978 [IT] Italy ................ 24857 A/78

[51] Int. Cl.³ .......................................... C07D 237/22
[52] U.S. Cl. .......................................... 544/241; 71/92
[58] Field of Search .......................................... 544/241

[56] References Cited

FOREIGN PATENT DOCUMENTS 1124398  8/1968  United Kingdom .................... 544/241

OTHER PUBLICATIONS

Reichenedir et al., Chem. Abs. 77, 126667f.

*Primary Examiner*—Mark L. Berch
*Attorney, Agent, or Firm*—Young & Thompson

[57] ABSTRACT

The compound 5-amino-4-chloro-2-phenyl-3(2H)-pyridazinone free from 5-chloro-4-amino-2-phenyl-3(2H)-pyridazinone is used as selective weed-killer in a remarkably more efficacious and remarkably less phytotoxic way than the presently known "pyrazon" (mixture of 5-amino-4-chloro-2-phenyl-3(2H)-pyridazinone and 5-chloro-4-amino-2-phenyl-3(2H)-pyridazinone). The 5-amino-4-chloro-2-phenyl-3(2H)-pyridazinone is obtained from pyrazon by treating said pyrazon with a mineral acid of pre-fixed concentration, obtaining a suspension and filtering such a suspension. The use thereof as weed-killer is carried out in suitable formulations.

6 Claims, No Drawings

5-AMINO-4-CHLORO-2-PHENYL-3(2H)-PYRIDAZINONE FREE FROM 5-CHLORO-4-AMINO-2-PHENYL-3(2H)-PYRIDAZINONE, AS A SELECTIVE WEED-KILLER

BACKGROUND OF THE INVENTION

It is known to those skilled in the art that the amination of 4,5-dichloro-2-phenyl-3(2H)-pyridazinone leads through the two simultaneous reactions:

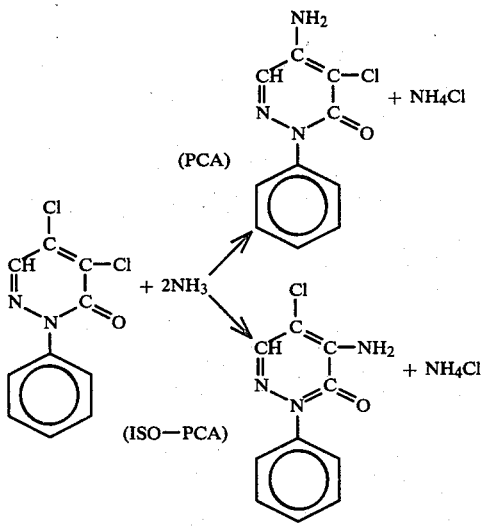

to the formation of commercial PYRAZON, that is a product constituted by a mixture of two isomers, one of which, 5-AMINO-4-CHLORO-2-PHENYL-3(2H)-PYRIDAZINONE (also referred to hereinafter by the abbreviation PCA) is active as a selective weed-killer for agricultural use while the second, 4-AMINO-5-CHLORO-2-PHENYL-3(2H)-PYRIDAZINONE (also referred to hereinafter by the abbreviation ISO-PCA) does not have any herbicidal activity (and the presence of which is therefore superfluous, if not harmful, when it is applied to the soil together with the first).

SUMMARY OF THE INVENTION

The main object of the present invention is to obtain improved herbicidal compositions for agricultural use having superior properties to those currently in use and, to this end, to obtain the isomer (PCA) which is active as a selective herbicide or weed-killer practically free from the inactive isomer (ISO-PCA).

This object is achieved by means of the present invention by making use of the property, which is totally unexpected and not known from the chemical literature, that in mineral acids, such as hydrochloric and sulphuric acid, of suitable concentration a distinct diversity of solubility of the two isomers PCA and ISO-PCA occurs.

On the basis of this property, the present invention provides a process for obtaining 5-amino-4-chloro-2-phenyl-3(2H)-pyridazinone (PCA) free from 5-chloro-4-amino-2-phenyl-3(2H)-pyridazinone (ISO-PCA) from commercial Pyrazon, that is from a mixture of the said two isomeric compounds, which is characterized in that commercial Pyrazon is treated with a mineral acid of suitable concentration, a suspension being obtained, and the suspension obtained is filtered to derive the desired product (PCA).

The mineral acid employed will preferably be hydrochloric acid with a concentration higher than 30% or sulphuric acid with a concentration higher than 60%, either in a proportion preferably of 1:2.5 weight-/volume between the commercial Pyrazon and the mineral acid in solution.

By this process the product 5-amino-4-chloro-2-phenyl-3(2H)-pyridazinone free from the isomer 4-chloro-5-amino-2-phenyl-3(2H)-pyridazinone is obtained with a melting point of 204°–206° C. This product proves unexpectedly to be of a toxicity lower than that of the mixture of the two starting isomers. In fact, tests carried out have shown that the product obtained by means of the present invention has a LD 50:4110 mg/kg in rats against LD 50:2292 mg/kg in rats of the starting commercial Pyrazon.

It is considered preferable that the process according to the invention will also include the additional stage of recovering the isomer (ISO-PCA) remaining in solution by means of dilution of the mother filtration liquors with water in the proportion of 1:1 and subsequent filtration of the diluted solution.

To obtain improved herbicidal compositions, the present invention provides for a suitable formulation of herbicidal compositions containing as active substance the isomer (PCA) obtained by the above-claimed process. These compositions may be in the form of wettable powders or water-dispersible pastes or of microgranules and will be used in agriculture especially on crops of beetroot and sugar beet in pre-sowing, pre-emergence and post-emergence treatments.

In fact, experiments carried out for the selective eradication of weeds from agricultural crops, and in particular sugar beet, have enabled it to be ascertained unexpectedly that herbicidal formulations containing pure PCA have, with respect to those containing the mixture of the two isomers, a greater effectiveness on infesting plants and a lesser phytotoxicity for the crops, especially if they are used in postemergence treatments.

The possibility of producing herbicidal compositions containing pure PCA which, for equality of organic substance employed, have a greater content of active substance, moreover enables substantial advantages to be obtained from the ecological point of view, inasmuch as it is possible in this case to avoid distributing ISO-PCA, an organic compound useless for practical purposes, over the soil, with a consequent lower pollution of the environment.

Solid economic advantages are also achieved because of the smaller amounts of chemical additives used, without any reduction in the biological efficiency of the herbicidal compositions.

DESCRIPTION OF THE PREFERRED EMBODIMENT

Going back to considering in greater detail the process for obtaining the isomer (PCA) of commercial Pyrazon, the treatment of the starting mixture with mineral acid will be examined.

If the mixture of isomers, PCA and ISO-PCA, which forms commercial Pyrazon is treated with hydrochloric acid, it can be established that the concentration of this acid must be higher than 30%: more precisely, fully satisfactory results have been obtained with concentrations ranging between 31% and 37%. In hydrochloric acid of this concentration, in fact, the isomer ISO-PCA dissolves without any difficulty, while the isomer PCA is very little soluble, for which reason it is separated by simple filtration and washing to neutrality.

The separation is so selective that the PCA is obtained with a titre higher than 96% and, by using a suitable ratio of solid/hydrochloric acid, preferably a ratio of 1:2.5 weight/volume, yields higher than 95% are obtained.

The isomer ISO-PCA dissolved in the mother liquors is recovered by dilution with $H_2O$ and subsequent filtration. If hydrochloric acid with concentrations lower than 30% is used, the titre of the product rapidly gets worse, inasmuch as there is insufficient solubilization of the isomer ISO-PCA.

If the mixture of isomers, PCA and ISO-PCA, which forms commercial Pyrazon is treated with sulphuric acid, it can be established that the concentration of this acid must be higher than 60%: more precisely, the best results have been obtained with concentration ranging between 60% and 75%.

In sulphuric acid of this concentration the isomer ISO-PCA dissolves without any problems, while the isomer PCA is poorly soluble, for which reason it is easily separated by filtration and subsequent washing to neutrality.

With sulphuric acid of the concentration indicated, a product with a titre higher than 96% is obtained and, by using a suitable ratio of solid/sulphuric acid, preferably a ratio of 1:2.5 weight/volume, yields ranging between 85% and 90% are obtained.

If sulphuric acid in concentrations lower than 60% is used, there is a deterioration of the titre of the PCA obtained (inasmuch as there is insufficient solubilization of ISO-PCA), while if the concentration of 75% is exceeded there is a lowering of the yield of purified product (inasmuch as the isomer PCA also tends to dissolve in this case).

Some practical examples for performing the process according to the invention will now be given. These are obviously of a purely indicative nature and do not introduce any limitation of the invention itself.

Example 1 of Process 1000 ml of 32% HCl  d=1.16
are placed in a reaction vessel and then, in about half an hour,
400 g of commercial Pyrazon containing 86% of PCA, m.p. 185°–195° C.,
are fed in. Stirring is carried out for 4 to 6 hours at room temperature, the suspension is filtered and washing is carried out with
400 ml of 32% HCl
and then with $H_2O$ to neutrality. The cake is dried and there is obtained:
340 g of purified PCA with a titre of 97% - m.p. 204°–206° C. Yield in product 100%=96% of the theoretical.

The mother filtration liquors, to which the hydrochloric acid used for washing has been added are diluted with
1400 ml of water.
The mixture is left to be stirred until complete precipitation of the ISO-PCA occurs and then filtration and washing with water to neutrality are carried out.

Example 2 of Process 1000 ml of 32% HCl  d=1.16
are placed in a reaction vessel and then, in about half an hour,
400 g of commercial Pyrazon containing 84% of PCA
are added. The procedure carried out is as in Example 1 and there is obtained:
331 g of purified PCA with a titre of 96.5% - m.p. 204°–206° C. Yield in product 100%=95% of the theoretical.

Example 3 of Process 1000 ml of 37% HCl d=1.184
are placed in a reaction vessel and then, in about half an hour,
400 g of commercial Pyrazon containing 86% of PCA are added. Stirring is carried out for 2 to 4 hours at room temperature, the suspension is filtered and washing is carried out with
400 ml of 37% HCl.
The procedure carried out is as in Example 1 and there is obtained:
326 g of purified PCA with a titre of 98%.
Yield in product 100%=93% of the theoretical.

Example 4 of Process 1000 ml of 28% HCl  d=1.14
are placed in a reaction vessel and then, in about half an hour,
400 g of commercial Pyrazon containing 86% of PCA are added. Stirring is carried out for 6 hours at room temperature and then the procedure is as in Example 1. There is obtained:
378 g of 89% PCA.
It can be seen clearly how the 28% concentration of the hydrochloric acid is not sufficient to achieve good purification of the commercial Pyrazon.

Example 5 of Process 2000 ml of 32% HCl  d=1.16
are placed in a reaction vessel and then, in about half an hour,
400 g of commercial Pyrazon containing 86% of PCA are added. The procedure as in Example 1 is then followed, to obtain:
319 g of purified PCA with a titre of 97%.
Yield in product 100%=90% of the theoretical.

Example 6 of Process 1000 ml of 70% sulphuric acid
are placed in a reaction vessel and then, in about half an hour,
400 g of commercial Pyrazon containing 86% of PCA
are fed in at room temperature. Stirring is carried out for 4 hours at room temperature, the suspension is filtered and washing is carried out with
400 ml of 70% $H_2SO_4$
The cake is taken up in water and filtering and washing to neutrality are carried out. After drying there is obtained:
314 g of purified Pyrazon containing 96.5% of PCA
Purification yield: 88% of the theoretical.

Example 7 of Process

The same procedure as in Example 6 is followed, but using
1000 ml of 55% H$_2$SO$_4$.
There is obtained:
360 g of Pyrazon containing 90% of PCA.

As can be seen, with H$_2$SO$_4$, of a concentration lower than 60%, a product (PCA) of insufficient purity for the purposes which are proposed here is obtained.

Example 8 of Process

The same procedure as in Example 6 is followed, but using
1000 ml of 80% H$_2$SO$_4$.
There is obtained:
226 g of purified Pyrazon containing 98.8% of PCA. Purification yield: 65% of the theoretical.

As can be seen, with H$_2$SO$_4$ of a concentration higher than 75%, a product (PCA) of very high purity is obtained, but the yield is inadequate.

As it has been said, the purified Pyrazon (PCA) is useful for producing improved herbicidal compositions, to prepare which it is expedient that it is formulated in suitable manner by techniques known to those skilled in the art, the compositions being produced either as wettable powder or as water-dispersible paste or else as microgranules.

For wettable powder, it is necessary that after mixing of the active substance and the inert substances they are subjected to grinding with suitable mills (e.g. an air jet mill) so as to obtain formulations having very fine particles, for example with a diameter smaller than 15 microns and, if possible, even smaller than 5 microns.

For water-dispersible paste, after mixing of the active substance and the inert substances, for the most part liquid substances, the composition is subjected to intensive grinding with suitable equipment (for example, in a bead or sand mill) so as to obtain a size of the solid particles which is smaller than 10 microns, if possible smaller than 2 microns. The following Examples relate to the formulation of herbicidal compositions according to the invention and are obviously only of an illustrative and non-limitative nature.

Formulation Example I

A wettable powder containing 77.6% of active substance is prepared by mixing:

| | |
|---|---|
| Purified Pyrazon containing 97% of PCA | 80 g |
| Sodium lauryl sulphonate | 2 g |
| Sodium polymethacrylate | 2 g |
| Sodium lignin sulphonate | 2 g |
| Kaolin in very fine powder form | 3 g |
| Colloidal silica | 10 g |
| total | 100 g |

Formulation Example II

A water-dispersible paste is prepared by mixing:

| | |
|---|---|
| Purified Pyrazon containing 97% of PCA | 532 g |
| Butyl alcohol condensed with ethylene oxide | 80 g |
| Homopolysaccharide | 2 g |
| Dimethylpolysiloxane | 5 g |
| Ethylene glycol | 70 g |
| Deionised water | 311 g |
| total | 1000 g |

The effectiveness of the herbicides obtained with the compositions of which the formulation has been discussed hereinbefore can be made clear by considering the results of the following Examples of application, which are also given purely by way of illustration and non-limitatively.

Example of Application I

In a field intended for sowing sugar beet and ready for sowing there are distributed, by spraying with conventional equipment, herbicidal compositions containing either purified Pyrazon containing 97% of PCA or commercial Pyrazon containing 84% of PCA which are formulated both as wettable powders and as water-dispersible pastes as indicated in the foregoing Formulation Examples I and II, in such manner as to employ the same amount of active substance per hectare, as stated in Table I given hereinafter.

After the distribution of the weed-killers or herbicides, they are incorporated in the surface of the soil to a depth of 3 to 4 cm by suitable harrowing (incorporated pre-sowing treatment).

Mechanical sowing of the MARIBO UNICA variety of beet is thereafter effected.

Similarly to the pre-sowing treatment, after sowing, distribution of the same weed-killers is carried out at the same rates of use before emergence of the crop from the surface of the soil (pre-emergence treatment).

The same herbicidal treatments are also effected in this way when the crop has a development of 4 or 5 leaves and the infesting weeds are in a juvenile stage of development.

From the data obtained and given in Table I it can be observed how the formulations containing Pyrazon with 97% of PCA provide optimum results, superior to those obtainable with formulations containing Pyrazon with 84% of PCA, when the two types of formulations are used at equivalent rates of active substance.

In Table I, the numbers relating to the effectiveness or the phytotoxicity have the following significance:

0 = No phytotoxicity on the crop or effectiveness on the weeds

100 = Total destruction of the crop or the weeds.

Intermediate values represent intermediate levels of effectiveness or phytotoxicity.

TABLE I

Effectiveness and phytotoxicity of formulations containing PYRAZON with 97% of PCA and PYRAZON with 84% of PCA used in accordance with various techniques for eradicating weeds from sugar beet.

| Formulations employed | Rates Kg/Ha | PRE-SOWING | | | PRE-EMERGENCE | | | POST-EMERGENCE | | |
|---|---|---|---|---|---|---|---|---|---|---|
| | | B | C | S | B | C | S | B | C | S |
| (1) WETTABLE POWDERS | | | | | | | | | | |
| (a) with PYRAZON containing 97% PCA | 4.000 Pyrazon 65% = 2.600 PCA | 0 | 91 | 100 | 0 | 97 | 100 | 0 | 83 | 100 |
| (b) with PYRAZON containing 84% PCA | 3.350 Pyrazon 77.6% = 2.600 PCA | 0 | 86 | 100 | 0 | 90 | 100 | 0 | 72 | 100 |

TABLE I-continued

Effectiveness and phytotoxicity of formulations containing PYRAZON with 97% of PCA and PYRAZON with 84% of PCA used in accordance with various techniques for eradicating weeds from sugar beet.

| Formulations employed | Rates Kg/Ha | PRE-SOWING B | PRE-SOWING C | PRE-SOWING S | PRE-EMERGENCE B | PRE-EMERGENCE C | PRE-EMERGENCE S | POST-EMERGENCE B | POST-EMERGENCE C | POST-EMERGENCE S |
|---|---|---|---|---|---|---|---|---|---|---|
| (2) WATER-DISPERSIBLE PASTES | | | | | | | | | | |
| (a) with PYRAZON containing 97% PCA | 5.000 Pyrazon Paste = 2.580 PCA | 0 | 95 | 100 | 0 | 99 | 100 | 0 | 85 | 100 |
| (b) with PYRAZON containing 84% PCA | 6.000 Pyrazon Paste = 2.580 PCA | 0 | 90 | 100 | 0 | 94 | 100 | 0 | 77 | 100 |
| CONTROL FIELD WITHOUT HERBICIDAL TREATMENTS | | 0 | 0 | 0 | 0 | 0 | 0 | 0 | 0 | 0 |

B = MARIBO UNICA SUGAR BEET VARIETY
C = CHENOPODIUM ALBUM
S = STELLARIA MEDIA

Example of Application II

Monogerm beets of the Monyx and Monogem varieties are sown in two fields and, after these crops or cultures have reached the stage of two true leaves, herbicidal treatments are carried out either with Pyrazon containing 84% of PCA or with Pyrazon containing 97% of PCA, at the rates indicated in the following Table II, the weed-killers being distributed uniformly over the entire surface of the fields with a conventional spraying pump for agricultural weed eradication equipped with a nozzle bar with a distributor.

30 days after the herbicidal treatment results may be observed. From the data obtained, given in Table II, it can be observed how the formulations containing Pyrazon with 97% of PCA present an unexpected lesser phytotoxicity for the beets and an as unexpected greater effectiveness on the infesting weeds compared with similar formulations containing Pyrazon with 84% of PCA and employed in equivalent amounts of active substance.

In the following Table II, the numbers relating to the effectiveness and phytotoxicity have the following significance:

0 = no phytotoxicity on the crops or effectiveness on the weeds

100 = total destruction of the crops or the weeds.

Intermediate values represent intermediate levels of phytotoxicity and effectiveness.

I claim:

1. Process for obtaining 5-amino-4-chlor-2-phenyl-3(2H)-pyridazinone (PCA) free from 5-chloro-4-amino-2-phenyl-3(2H)-pyridazinone (ISO-PCA) starting from commercial Pyrazon, that is from a mixture of the said two isomeric compounds, characterised in that commercial Pyrazon is treated with a mineral acid of suitable concentration, said concentration being suitable to dissolve the ISO-PCA but very little of the PCA, thereby to form a suspension of PCA in a solution of ISO-PCA, and thereafter filtering said suspension to remove PCA in the form of particles from said solution.

2. Process as claimed in claim 1, wherein the mineral acid with which commercial Pyrazon is treated is hydrochloric acid with a concentration higher than 30%.

3. Process as claimed in claim 1, wherein the mineral acid with which commercial Pyrazon is treated is sulphuric acid with a concentration higher than 60%.

4. Process as claimed in claim 1, wherein the ratio between the commercial Pyrazon and mineral acid is not higher than 1:2.5 weight/volume.

5. Process as claimed in claim 2, wherein the concentration of the hydrochloric acid varies from 31% to 37% and the ratio between the commercial Pyrazon and the hydrochloric acid is 1:2.5 weight /volume.

6. Process as claimed in claim 3, wherein the concentration of the sulphuric acid varies from 60% to 75% and the ratio between the commercial Pyrazon and the sulphuric acid is 1:2.5 weight/volume.

* * * * *

TABLE II

Effectiveness and phytotoxicity of formulations containing PYRAZON with 97% of PCA and PYRAZON with 84% of PCA used in post-emergence in the eradication of weeds from sugar beet.

| Formulations employed | Rates Kg/Ha | Type of beet Monyx | Type of beet Monogem | Amaranthus Retroflexus | Chenopodium Album |
|---|---|---|---|---|---|
| (1) WETTABLE POWDERS | | | | | |
| (a) with Pyrazon containing 97% | 1.625 Pyrazon 80% = 1.300 PCA | 0 | 5 | 5 | 100 |
| | 2.438 Pyrazon 80% = 1.950 PCA | 5 | 15 | 100 | 100 |
| (b) with Pyrazon containing 84% | 2.000 Pyrazon 65% = 1.300 PCA | 5 | 10 | 0 | 70 |
| | 3.000 Pyrazon 65% = 1.950 PCA | 20 | 20 | 40 | 100 |
| (2) WATER-DISPERSIBLE PASTES | | | | | |
| (a) with Pyrazon containing 97% | 2.600 Pyrazon paste = 1.300 PCA | 0 | 0 | 50 | 100 |
| | 3.900 Pyrazon paste = 1.950 PCA | 10 | 10 | 100 | 100 |
| (b) with Pyrazon containing 84% | 3.000 Pyrazon paste = 1.300 PCA | 25 | 20 | 20 | 30 |
| | 4.350 Pyrazon paste = 1.950 PCA | 30 | 30 | 45 | 55 |
| Control beets without treatments | | 0 | 0 | 0 | 0 |